United States Patent [19]

Stein

[11] Patent Number: 5,405,374
[45] Date of Patent: Apr. 11, 1995

[54] TRANSVENOUS DEFIBRILLATION LEAD AND METHOD OF USE

[75] Inventor: Paul M. Stein, Maple Grove, Minn.

[73] Assignee: Medtronic, Inc., Minneapolis, Minn.

[21] Appl. No.: 112,506

[22] Filed: Aug. 25, 1993

[51] Int. Cl.⁶ .................................... A61N 1/04
[52] U.S. Cl. ............................ 607/122; 607/127; 607/128; 128/642
[58] Field of Search ............... 128/642, 119, 122, 123, 128/125–128

[56] References Cited

U.S. PATENT DOCUMENTS

| Re. 27,757 | 9/1973 | Mirowski . | |
|---|---|---|---|
| 3,729,008 | 4/1973 | Berkovits . | |
| 3,942,536 | 3/1976 | Mirowski . | |
| 4,106,512 | 8/1978 | Bisping . | |
| 4,136,703 | 1/1979 | Wittkampf | 607/125 |
| 4,154,247 | 5/1979 | O'Neill | 607/125 |
| 4,161,952 | 7/1979 | Kinney . | |
| 4,355,646 | 10/1982 | Kallok . | |
| 4,394,866 | 7/1983 | Hughes | 607/125 |
| 4,401,126 | 8/1983 | Reenstierna | 607/125 |
| 4,402,330 | 9/1983 | Lindemans . | |
| 4,481,953 | 11/1984 | Gold . | |
| 4,641,656 | 2/1987 | Smits . | |
| 4,708,145 | 11/1987 | Tacker, Jr. . | |
| 4,727,877 | 3/1988 | Kallok . | |
| 4,934,049 | 6/1990 | Kiekhafer . | |
| 4,951,687 | 8/1990 | Ufford . | |
| 4,953,551 | 9/1990 | Mehra . | |
| 5,007,436 | 4/1991 | Smits . | |
| 5,010,894 | 4/1991 | Edhag . | |
| 5,133,365 | 7/1992 | Heil, Jr. . | |
| 5,144,960 | 9/1992 | Mehra . | |

FOREIGN PATENT DOCUMENTS 2615107  11/1988  France .................. 607/119

Primary Examiner—Lee S. Cohen
Assistant Examiner—Jeffrey R. Jastrzab
Attorney, Agent, or Firm—Reed A. Duthler; Harold R. Patton

[57] ABSTRACT

A defibrillation lead for location in a human heart, having an elongated lead body defining a generally straight segment extending from its proximal end and a curved segment extending distally from the straight segment. The curved segment has a sigmoidal configuration including a two or more alternating, generally coplanar curves, and carries an elongated defibrillation electrode extending along its length. A stylet is provided for straightening the curved segment prior to implant.

12 Claims, 2 Drawing Sheets

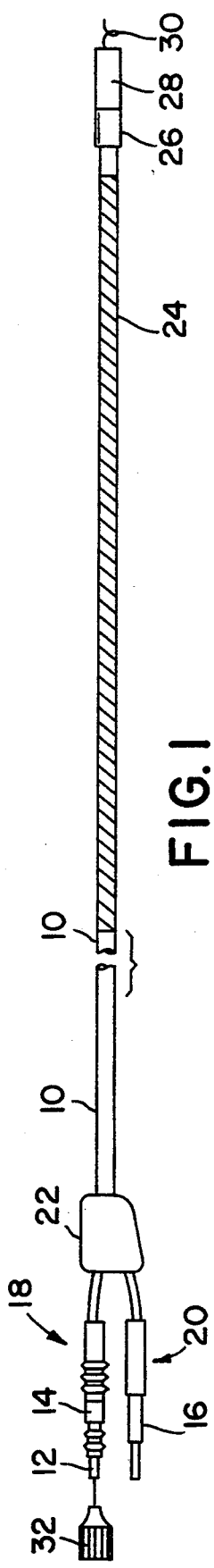
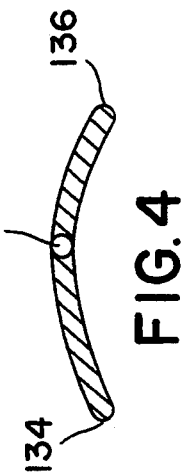
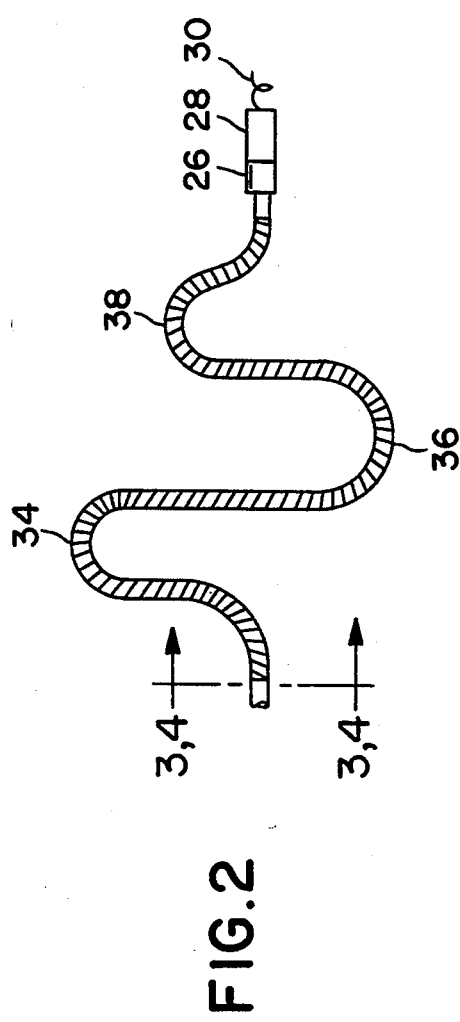

TRANSVENOUS DEFIBRILLATION LEAD AND METHOD OF USE

BACKGROUND OF THE INVENTION

The present invention relates to medical electrical leads generally, and more particularly to implantable defibrillation electrodes and leads.

Early concepts of implantable defibrillators, such as disclosed in U.S. Pat. Re. No. 27,652 by Mirowski et al., envision an electrode system employing a ventricular endocardial electrode and a plate electrode mounted to the heart directly, subcutaneously, or to the skin. However, it has long been recognized that a totally transvenous system would be desirable to simplify the use of implantable defibrillators. One such system is suggested in U.S. Pat. No. 3,942,536 by Mirowski et al., which discloses a transvenous lead having electrodes intended for location in the right ventricular apex and in the superior vena cava. Such systems were eventually tested in human beings, with some success. However, currently available implantable defibrillators typically employ epicardial patch electrodes, alone, or in conjunction with transvenous electrodes.

While systems employing epicardial patch electrodes are workable, a thoracotomy is required to apply the epicardial electrodes. It is generally believed that it would be desirable to produce an implantable defibrillation system which entirely avoids the necessity of a thoracotomy, and there has been substantial work directed toward development of such systems, as disclosed in U.S. Pat. No. 4,727,877 issued to Kallok, U.S. Pat. No. 4,708,145 issued to Tacker et al. and as disclosed in U.S. application Ser. No. 07/284,957 filed Dec. 15, 1988 by Mehra, for an "Endocardial Defibrillation Electrode System". Other endocardial defibrillation electrodes are disclosed in U.S. Pat. No. 4,481,953 issued to Gold et al., U.S. Pat. No. 4,161,952 issued to Kinney et al., U.S. Pat. No. 4,934,049 issued to Kiekhafer et al. and in U.S. patent application Ser. No. 07/479,928, filed Feb. 14, 1990 by Holleman et al., for an "Implantable Electrode and Method for Fabrication". The Kinney, Gold, and Kiekhafer patents and the Holleman et al. application all disclose endocardial defibrillation leads employing defibrillation electrodes fabricated from elongated coils of biocompatible metal, mounted exposed to the exterior of the defibrillation lead, for location in the right ventricle and other locations within the heart. U.S. Pat. No. 4,641,656 issued to Smits and the above cited Mehra application both disclose a variety of endocardial defibrillation electrodes intended for use in the atrium, ventricle, and coronary sinus, all of which employ electrodes taking the form of elongated coils of conductive biocompatible metals.

Recently, it has been recognized that increasing the surface area of defibrillation electrodes located in the right ventricle may be one way to provide reduced defibrillation thresholds. U.S. Pat. No. 5,144,960 issued to Mehra et al. accomplishes an increased surface area by means of a bifurcated lead having two elongated electrode coils located in the right ventricle. U.S. Pat. No. 5,010,894 issued to Edhag also discloses right ventricular defibrillation leads having multiple electrode coils having differing configurations. U.S. Pat. No. 5,133,365 discloses a right ventricular defibrillation lead having a spiral configuration and U.S. Pat. No. 5,007,436 discloses a right ventricular lead having a J-shaped configuration.

SUMMARY OF THE INVENTION

The present invention is directed toward the provision of an endocardial defibrillation lead particularly optimized for use in conjunction with one or more epicardial patch or subcutaneous electrodes. However, the electrode may also be used in conjunction with other endocardial electrodes, such as superior vena cava or coronary sinus electrodes.

The lead is provided with an elongated lead, non-diverging lead body, including a first, generally straight segment intended to extend from a proximal end coupled to an implanted defibrillation pulse generator to a second, curved segment, carrying an elongated defibrillation electrode. The distal end of the lead carries one or more electrodes for cardiac pacing and for sensing of electrical activity of the ventricle.

The shape of the curved segment is specifically optimized to provide an electrode having both increased surface area and improved distribution of electrode surface within the right ventricular cavity as compared to prior ventricular defibrillation electrodes. The shape of the curved segment is also adapted to allow appropriate location of sensing electrodes within the ventricle and to provide a simple technique for implantation and electrode deployment.

A lead according to the present invention accomplishes the objectives stated above by means of a curved segment which has a sigmoidal configuration, comprising a plurality of alternating, generally coplanar curves. The lead is sized and configured such that the defibrillation electrode extends across the right ventricular cavity, between the right ventricular apex and the tricuspid valve, generally parallel to the septum of the heart. The curved segment is straightened for implant by means of a styler, which is removed gradually after location of the distal end of the lead in the ventricular apex, allowing the curves of the curved segment to be sequentially and alternately disposed adjacent the anterior and posterior walls of the right ventricle. The electrode as implanted extends across the right ventricle, near the septum. The defibrillation electrode as implanted is thus in relatively close proximity to the majority of the muscle mass of the right ventricle and septum. In conjunction with an appropriately located subcutaneous or left ventricular epicardial electrode, this electrode configuration also allows the physician to place the majority of the left ventricular muscle mass directly between the defibrillation electrodes.

BRIEF DESCRIPTION OF THE DRAWINGS

FIG. 1 is a plan view of a lead according to the present invention, straightened by insertion of a stylet.

FIG. 2 is a plan view of the distal segment of a lead according to the present invention, after removal of the stylet.

FIG. 3 is a view looking distally down the distal segment of a first embodiment of the lead of FIG. 2.

FIG. 4 is a view looking distally down the distal segment of a second embodiment of the lead of FIG. 2.

DETAILED DESCRIPTION OF THE PREFERRED EMBODIMENTS

Figure 6:
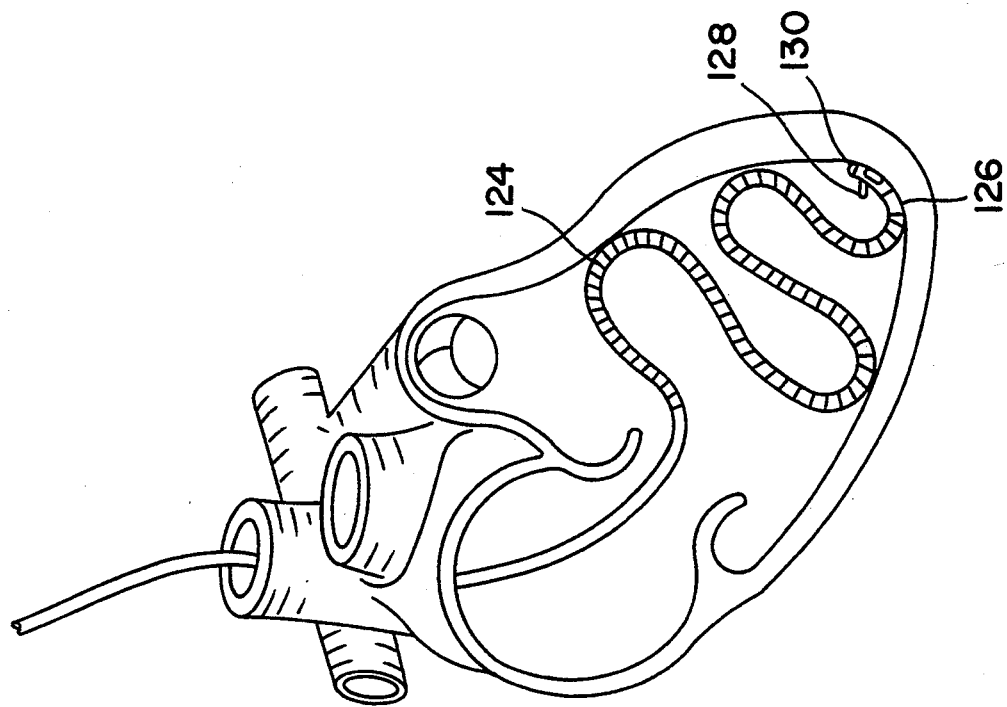
FIG. 6 illustrates a third embodiment of a lead according to the present invention as implanted in the right ventricle.

FIG. 1 illustrates the distal end of a lead according to the present invention. The distal end of the lead is provided with a pacing and sensing electrode assembly, including an extendable helix electrode 30, mounted retractably within an insulative electrode head 28, and a ring electrode 26. Defibrillation electrode coil 24 extends proximally from a point adjacent the ring electrode 26.

Insulative sheath 10 covers the lead body and contains three concentric coiled conductors, separated from one another by tubular insulative sheaths. This tripolar arrangement is illustrated in more detail in U.S. Pat. No. 4,355,646, issued to Kallok et al. incorporated herein by reference in its entirety. As set forth in the cited Kallok et al. patent, the insulative sheaths employed in the present lead may be made of an implantable polyurethane. However, in some embodiments, the sheaths may be made of silicone rubber or other implantable, flexible plastic. The conductor coils may be made of Drawn Brazed Strand wire (DBS), previously used in cardiac pacing leads or may be another implantable metal such as MP35N alloy, also commonly used in pacing leads.

The outermost of the three conductor coils within sheath 10 is coupled to the proximal end of electrode coil 28 and the middle coil within lead body 10 is coupled to ring electrode 26. The innermost coil is mounted rotatably within an insulative sheath separating the innermost coil from the middle coil, and is mechanically and electrically coupled to helix electrode 30, which is retractably mounted within electrode head 28. Rotation of the innermost conductor coil causes rotation of electrode 30 and advancement of electrode 30 out the distal end of electrode head 28. Electrode 30 may be screwed into the tissue of the right ventricle of the heart, and is used to anchor the lead. The electrode head 28, electrode 30, and the inner most conductor coil employed to rotate the helical electrode 30 are described in more detail in U.S. Pat. No. 4,106,512, issued Aug. 15, 1978 to Bisping, incorporated herein by reference in its entirety.

Electrode 24 may be mounted around sheath 10 and bonded thereto by means of a backfill of insulative plastic, as described in U.S. Pat. No. 4,934,049 issued to Kiekhafer et al. on Jun. 19, 1990, and incorporated herein by reference in its entirety. As an alternative, sheath 10 may be fabricated of a polyurethane or other heat flowable material, expanded against the interior of the electrode coils under pressure and heated to allow the material of the sheath to flow between the electrode coils, as illustrated in U.S. patent application Ser. No. 07/479,928, filed on Feb. 14, 1990 for an "Implantable Electrode and Method for Fabrication" by Holleman et al., also incorporated herein by reference in its entirety. Alternatively, electrode coil 24 may be fabricated using the techniques illustrated in the above cited Kinney or Gold patents. Electrode coil 24 is preferably made of platinum. However, as discussed in the references cited above, other implantable metals have been disclosed for use in such electrodes.

At the proximal end of the lead a connector assembly is provided. The connector assembly includes a standard IS-1 compatible in-line bipolar connector assembly 18, carrying connector pin 12 and electrode ring 14. Electrode 12 is coupled to the inner most of the three coiled conductors and may be rotated in order to rotate the innermost coiled conductor to advance helical electrode 30. Connector ring 14 is coupled to ring electrode 26 by means of the middle coiled conductor. A stylet 32 is shown inserted through the central bore of connector pin 12, and extends to the distal end of the lead. The styler 32 maintains the lead in a generally straight configuration, as it is passed through the vascular system and into the right ventricle. An appropriate structure for producing an IS-1 compatible, rotatable connector pin assembly as illustrated may be found in U.S. Pat. No. 4,951,687 issued to Ufford et al. on Aug. 28, 1990, incorporated herein by reference in its entirety.

A high voltage electrical connector 20 carries stepped connector pin 16 which is coupled to defibrillation electrode 24 by the outermost of the three coiled conductors within the lead body. Connector assemblies 18 and 20 are coupled to lead body by means of a Y fitting 22. The connector assemblies and pins illustrated are exemplary, and the specific connector assemblies and geometries chosen for use in conjunction with the present invention will of course depend upon the brand and manufacture of the implantable defibrillator to which they are intended to be attached.

FIG. 2 shows the distal end of the lead of FIG. 1, with the styler 32 (FIG. 1) removed. With the stylet removed, it can be seen that a lead assumes a tapered sigmoidal configuration, similar to a damped sinusoidal waveform. However, a non-tapered sigmoidal configuration is also believed workable. The electrode, as deployed, includes three of curves 34, 36, and 38 of alternating directions (i.e. curved right, curved left, curved right, etc.), which are generally coplanar to one another, with the more distal curves diminishing in their lateral extension. Configurations employing only two curved segments or more than three curved segments are also believed workable. As illustrated, electrode head 28 extends from the curved segment generally along the axis of straight segment of the lead. However, other configurations and orientations for the connector head assembly 28 are also believed workable.

FIGS. 3 and 4 show a view of the deployed electrode illustrated in FIG. 2, looking distally down the lead body. The lead body is visible in cross-section at 40, with curves 34 and 36 extending laterally therefrom, generally falling within a single plane. An alternative configuration is illustrated in FIG. 4, in which the lead body is visible in cross-section at 140, with sigmoidal curves 134 and 136 extending laterally therefrom. However, in the embodiment of FIG. 4, the electrode as deployed falls within a curved planar surface, similar to the outer surface of a cylinder. As implanted, the concave side of the curved surface defined by the electrode would be implanted facing the ventricular septum. After implant the lead may fibrose to the ventricular wall.

Figure 5:
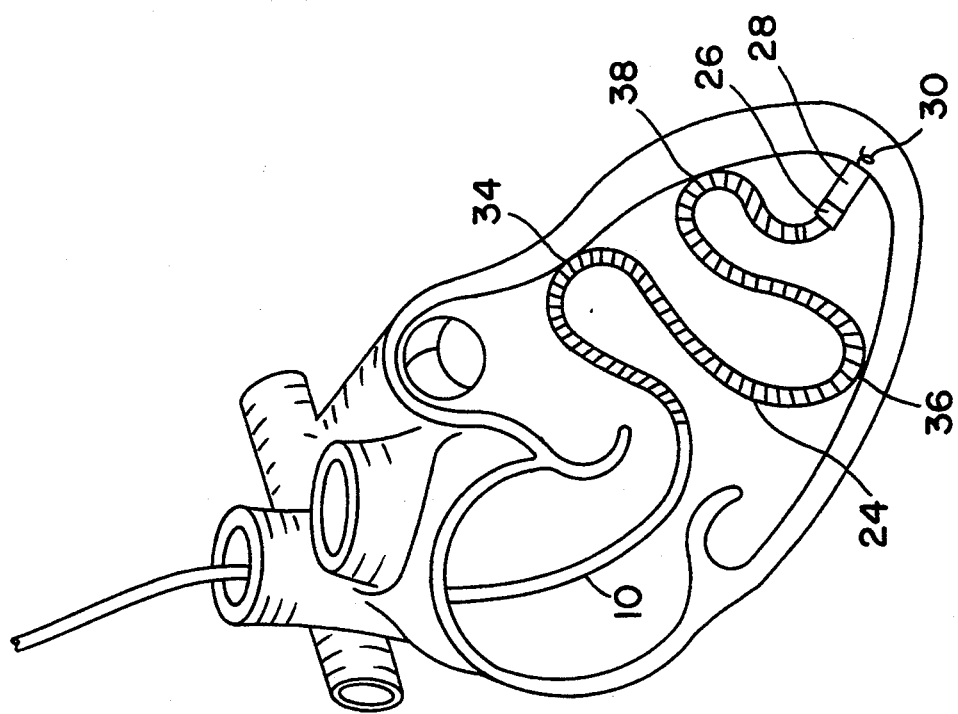
FIG. 5 illustrates a lead according to the present invention as implanted in the right ventricle.

FIG. 5 shows the lead of FIGS. 1 and 2 as implanted in the human heart. In FIG. 5, the right ventricular wall has been trimmed away, along a plane roughly parallel to the ventricular septum. The sectioned ventricular walls thus represent areas near the anterior and posterior edges of the septum. To implant the lead, the stylet is first inserted into the lead body, straightening it. The lead is then passed through the vascular system, through the superior vena cava, right atrium, tricuspid valve, and into the right ventricle. Helical electrode 30 is then screwed into the apex of the right ventricle, as illustrated. Thereafter, the styler is gradually removed, while observing the lead configuration on fluoroscope, to assure that the curved segments 34, 36, and 38 deploy themselves generally as illustrated, providing an electrode extending across the width of the right ventricle, with curves 34 and 38 generally adjacent to one of the anterior or posterior walls of the right ventricle, in the vicinity of the septum, with curve 36, adjacent to the other of the anterior or posterior ventricular walls. As illustrated, electrode 24 as deployed provides a substantially greater surface area than a corresponding straight body lead, and, provides a surface area which extends across the width of the right ventricle, as well as along the length of the right ventricle.

This electrode, in conjunction with a subcutaneous electrode, for example, located along the axillary line, provides an electrode system which places a majority of the muscle mass of the left ventricle directly between the defibrillation electrodes. Alternatively, a left ventricular epicardial patch electrode might be employed. Recently, the use of the housing of the implantable defibrillator as electrode has been suggested. In this case, the defibrillator would be implanted pectorally, and a lead according to the present invention is also believed valuable in conjunction with such a device.

FIG. 6 is a view of an alternate embodiment of a lead according to the present invention. The lead as illustrated corresponds generally to the lead illustrated in FIGS. 1 and 2, and carries an elongated defibrillation electrode coil 124 located along a portion of the lead body having a sigmoidal configuration. Rather than an extendable helix as distal electrode, a non-penetrating electrode 130 is provided, in conjunction with a ring electrode 126. The electrode 130 is maintained in its location in the apex of the heart by means of pliant tines 128, similar to those conventionally used on cardiac pacing leads. As illustrated, the overall configuration of the curved segment of the lead illustrated in FIG. 6 differs somewhat from that illustrated in conjunction with the lead illustrated in FIGS. 1–5, in that the electrode assembly does not lie along or parallel to the axis of the straight segment of the lead body. A configuration similar to that illustrated in FIG. 6 may of course be employed in a lead otherwise as illustrated in FIGS. 1 and 2, employing an active fixation device.

The curved configuration illustrated in FIGS. 2–6 may be maintained by any of a number of known mechanisms. It may be maintained by means of molding insulative sheath 10 in the form of a curved tube, or otherwise imparting a predetermined curve to the sheath. For example, the techniques illustrated in U.S. Pat. No. 3,729,008 issued to Berkovitz, also incorporated herein by reference in its entirety may be adapted. Alternatively, the electrode coil 24 may be preformed to exhibit a curved configuration or the conductor coils located within insulative sheath 10 may be preformed to assume a curved configuration. An additional preformed curved coil devoted particularly to maintaining the curved configuration of the lead may also be used, as disclosed in U.S. Pat. No. 4,402,330, issued on Sep. 6, 1983 to Lindemans, also incorporated herein by reference in its entirety, may also be used to maintain the curved configuration.

In use, a pulse is delivered between electrode 24 and a subcutaneous electrode or an epicardial electrode. An implantable defibrillator may be used to deliver such a pulse. A specific example of a defibrillation pulse generator which may be used in conjunction with the present lead is disclosed in U.S. Pat. No. 4,953,551, issued to Mehra et al. on Sep. 4, 1990, incorporated herein by reference in its entirety.

The invention disclosed herein is also believed practicable in conjunction with leads which have additional features, or may delete certain features from the lead as illustrated. For example, the pacing and sensing electrodes located at the distal end of the straight leg of the lead may be in some cases omitted, physiologic sensors or additional electrodes may be added to the lead body, for example in the portion of the lead which passes through the atrium. Similarly, the use of active or passive fixation devices other than as disclosed may be employed to anchor the distal end of the lead. Similarly, while a particular mechanism is disclosed for straightening the curved segment of the lead, other mechanisms may also be employed to accomplish this function. As such, the disclosed lead configuration should be considered exemplary, rather than limiting, with regard to the interpretation of the following claims.

In conjunction with the above specification, I claim:

1. A defibrillation lead for location in a human heart, comprising:
    an elongated lead body having proximal and distal ends, said lead body having a first generally straight segment extending from its proximal end and a second curved segment extending distally from said first segment, said second segment having a sigmoidal configuration comprising a plurality of alternating, generally coplanar curves;
    an elongated electrode extending along said second segment;
    a first conductor located within said lead body, and coupled to said elongated electrode;
    first connector means, coupled to said first conductor, for electrically coupling said elongated electrode to an implantable defibrillator; and
    means for straightening said second segment.

2. A lead according to claim 1 wherein said straightening means comprises a stylet.

3. A defibrillation lead for location in a human heart, comprising:
    an elongated lead body having proximal and distal ends, said lead body having a first generally straight segment extending from its proximal end and a second curved segment extending distally from said first segment, said second segment having a tapered sigmoidal configuration comprising a plurality of alternating, generally coplanar curves;
    an elongated electrode extending along said second segment;
    a first conductor located within said lead body, and coupled to said elongated electrode; and
    first connector means, coupled to said first conductor, for electrically coupling said elongated electrode to an implantable defibrillator.

4. A lead according to claim 2 further comprising means for fixing the distal end of said lead body in the apex of the right ventricle of said heart.

5. A lead according to claim 2 wherein said curves generally lie within a curved planar surface.

6. A defibrillation lead for location in a human heart, comprising:
    an elongated lead body having proximal and distal ends, said lead body having a first generally straight segment extending from its proximal end and a second curved segment extending distally from said first segment, said second segment having a sigmoidal configuration comprising a plurality of alternating, generally coplanar curves;

an elongated electrode extending along said second segment;

a first conductor located within said lead body, and coupled to said elongated electrode;

first connector means, coupled to said first conductor, for electrically coupling said elongated electrode to an implantable defibrillator;

means for fixing the distal end of said lead body in the apex of the right ventricle of said heart; and means for straightening said second segment.

7. A defibrillation lead for location in a human heart, comprising:

an elongated lead body having proximal and distal ends, said lead body having a first generally straight segment extending from its proximal end and a second curved segment extending distally from said first segment, said second segment having a sigmoidal configuration comprising a plurality of alternating, generally coplanar curves, wherein said curves generally lie within a curved planar surface;

an elongated electrode extending along said second segment;

a first conductor located within said lead body, and coupled to said elongated electrode;

first connector means, coupled to said first conductor, for electrically coupling said elongated electrode to an implantable defibrillator; and means for straightening said second segment.

8. A defibrillation lead for location in a human heart, comprising:

an elongated lead body having proximal and distal ends, said lead body having a first generally straight segment extending from its proximal end and a second curved segment extending distally from said first segment, said second segment having a sigmoidal configuration comprising a plurality of alternating, generally coplanar curves;

an elongated electrode extending along a plurality of said curves;

a first conductor located within said lead body, and coupled to said elongated electrode;

first connector means, coupled to said first conductor, for electrically coupling said elongated electrode to an implantable defibrillator; and means for straightening said second segment.

9. A lead according to claim 8 wherein said straightening means comprises a stylet.

10. A defibrillation lead for location in a human heart, comprising:

an elongated lead body having proximal and distal ends, said lead body having a first generally straight segment extending from its proximal end and a second curved segment extending distally from said first segment, said second segment having a tapered sigmoidal configuration comprising a plurality of alternating, generally coplanar curves;

an elongated electrode extending along a plurality of said curves;

a first conductor located within said lead body, and coupled to said elongated electrode; and first connector means, coupled to said first conductor, for electrically coupling said elongated electrode to an implantable defibrillator.

11. A lead according to claim 8 or claim 10 further comprising means for fixing the distal end of said lead body in the apex of the right ventricle of said heart.

12. A lead according to claim 8 or claim 10 wherein said curved segments generally lie within a curved planar surface.

* * * * *